(12) United States Patent
Mishra et al.

(10) Patent No.: US 10,426,770 B2
(45) Date of Patent: Oct. 1, 2019

(54) PROCESS FOR THE PREPARATION OF LURASIDONE HYDROCHLORIDE

(71) Applicant: JUBILANT GENERICS LIMITED, Uttar Pradesh (IN)

(72) Inventors: Vaibhav Mishra, Uttar Pradesh (IN); Shailendr Dubey, Uttar Pradesh (IN); Kumber Singh, Uttar Pradesh (IN); Alka Srivastava Choudhary, Uttar Pradesh (IN); Dharam Vir, Uttar Pradesh (IN)

(73) Assignee: Jubilant Generics Limited, Noida, Uttar Pradesh (IN)

( * ) Notice: Subject to any disclaimer, the term of this patent is extended or adjusted under 35 U.S.C. 154(b) by 328 days.

(21) Appl. No.: 15/503,349

(22) PCT Filed: Oct. 9, 2015

(86) PCT No.: PCT/IN2015/050132
§ 371 (c)(1),
(2) Date: Feb. 10, 2017

(87) PCT Pub. No.: WO2016/059649
PCT Pub. Date: Apr. 21, 2016

(65) Prior Publication Data
US 2017/0246165 A1    Aug. 31, 2017

(30) Foreign Application Priority Data

Oct. 14, 2014  (IN) .......................... 2925/DEL/2014
Mar. 27, 2015  (IN) ............................ 856/DEL/2015

(51) Int. Cl.
| | |
|---|---|
| *A61K 31/496* | (2006.01) |
| *C07D 233/61* | (2006.01) |
| *C07D 417/12* | (2006.01) |
| *A61K 31/4178* | (2006.01) |
| *C07D 417/14* | (2006.01) |

(52) U.S. Cl.
CPC ........ *A61K 31/496* (2013.01); *A61K 31/4178* (2013.01); *C07D 233/61* (2013.01); *C07D 417/12* (2013.01); *C07D 417/14* (2013.01)

(58) Field of Classification Search
CPC .............. A61K 31/496; A61K 31/4178; C07D 233/61; C07D 417/12; C07D 417/14; C07D 48/10
See application file for complete search history.

(56) References Cited

U.S. PATENT DOCUMENTS

| | | |
|---|---|---|
| 5,532,372 A | 7/1996 | Saji et al. |
| 7,605,260 B2 | 10/2009 | Kakiya et al. |
| 8,853,395 B2 | 10/2014 | Zacche' et al. |

FOREIGN PATENT DOCUMENTS

| | | |
|---|---|---|
| CN | 102731512 A | 10/2012 |
| CN | 102746289 A | 10/2012 |
| CN | 102863437 A | 1/2013 |
| CN | 102952001 A | 3/2013 |
| CN | 103864774 A | 6/2014 |
| IN | 2306/MUM/2014 | 10/2014 |
| IN | 777/MUM/2013 | 5/2015 |
| JP | 4219696 B2 | 2/2009 |
| WO | WO 2011/136383 A1 | 11/2011 |
| WO | WO 2011/136384 A1 | 11/2011 |
| WO | WO 2012/131606 A1 | 10/2012 |
| WO | WO 2013/014665 A1 | 1/2013 |
| WO | WO 2014/037886 A1 | 3/2014 |

OTHER PUBLICATIONS

Tang et al., preparation method for lurasidone hydrochloride (CN 102746289 machine translation), 2012.*

* cited by examiner

*Primary Examiner* — Jafar F Parsa
(74) *Attorney, Agent, or Firm* — Knobbe, Martens, Olson & Bear LLP

(57) ABSTRACT

Disclosed herein is an improved process for the preparation of Lurasidone and its pharmaceutically acceptable salts via novel intermediate and use thereof for the preparation of an antipsychotic agent useful for the treatment of schizophrenia and bipolar disorder. Further, present invention provides a cost effective and eco-friendly process for producing Lurasidone hydrochloride of formula (I) substantially free of residual solvent(s) at industrial scale.

4 Claims, No Drawings

PROCESS FOR THE PREPARATION OF LURASIDONE HYDROCHLORIDE

FIELD OF THE INVENTION

This invention, in general, relates to an improved process for the preparation of lurasidone via novel compound of Formula (IV), pharmaceutically acceptable salts thereof and use thereof for the preparation of an antipsychotic agent useful for the treatment of schizopherenia and bipolar disorder. The present invention also relates to an improved process for the preparation of lurasidone hydrochloride substantially free of residual solvent(s).

BACKGROUND OF THE INVENTION

Lurasidone and its pharmaceutically acceptable salts like lurasidone hydrochloride is chemically, (3aR,4S,7R,7aS)-2-{(1R,2R)-2-[4-(1,2-benzisothiazol-3-yl)piperazin-1 yl-methyl] cyclohexylmethyl}hexahydro-4,7-methano-2H-isoindole-1,3-dione hydrochloride and has the structure represented by the Formula (I):

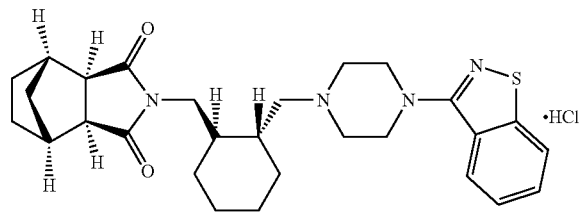

Formula-I

Lurasidone hydrochloride is marketed in the United States under the trade name Latuda®. Lurasidone and its pharmaceutically acceptable salts as well as process for their preparation was first disclosed in U.S. Pat. No. 5,532,372. The patent discloses the preparation of lurasidone hydrochloride using racemic trans 1,2-cyclohexane dicarboxylic acid. Racemic trans 1,2-cyclohexane dicarboxylic acid on reduction with lithium aluminium hydride in THF at reflux temperature forms 1,2-bis(hydroxymethyl)cyclohexane which is converted into racemic trans-1,2-bis(methanesulfonyloxymethyl)cyclohexane by reaction with methane sulfonyl halide. 1-(1,2-benzisothiazol-3-yl)piperazine on reaction with trans-1,2-bis (methanesulfonyloxymethyl) cyclohexane in the presence of sodium carbonate and acetonitrile forms trans-3a,7a-octahydroisoindolium-2-spiro-1'-[4'-(1,2-benzisothiazol-3-yl)]piperazine methanesulfonate which on reaction with bicyclo[2.2.1]heptane-2-exo-3-exo-dicarboximide in the presence of potassium carbonate, dibenzo-18-crown-6-ether and xylene on refluxing forms racemic lurasidone free base. The compound is obtained by column chromatography and then treated the resulting lurasidone free base with IPA.HCl in acetone to obtain racemic lurasidone hydrochloride. Resolution of racemic lurasidone hydrochloride is carried out using tartaric acid as resolving agent. The process involves use of lithium aluminium hydride which is highly pyrophoric reagent and is not to utilize the same on commercial scale due to its handling problems associated with its reactivity. Also, the use of the column chromatography for purification is not viable on commercial scale. Further the process involves the usage of dibenzo-18-crown-6-ether as a phase transfer catalyst which is costly material and in turn increases the cost of production. Carrying out the resolution in the last stages is difficult due to the presence of six chiral centres in lurasidone and is also not suitable for an industrial scale preparation as it affects the overall yield and cost of the manufacturing process.

Chinese patent application no. CN102731512 discloses a process for preparation of lurasidone which comprises reaction of racemic trans-1,2-bis(methanesulfonyloxymethyl) cyclohexane and 1-(1,2-benzisothiazol-3-yl)piperazine in toluene in the presence of sodium carbonate or potassium carbonate having particle size less than 200 micron and tetrabutyl ammonium bromide to give the intermediate trans-3a,7a-octahydroisoindolium-2-spiro-1'-[4'-(1,2-benzisothiazol-3-yl)]piperazinemethanesulfonate which on reaction with bicyclo[2.2.1]heptane-2-exo-3-exo-dicarboximide in toluene using potassium carbonate having particle size less than 200 micron forms racemic lurasidone free base. The racemic free base is converted into racemic hydrochloride salt using acetone and conc. hydrochloric acid. Racemic lurasidone hydrochloride is resolved by following the method disclosed in U.S. Pat. No. 5,532,372. The process involves resolution of product in the last stage which is not commercially viable as it affects the overall yield and cost of the manufacturing process.

Japanese patent no. JP4219696 discloses the resolution of trans 1,2-cycloheaxne dicarboxylic acid using (1S,2R)-(+)-norephedrine or (1R,2S)-(−)norephedrine to provide (R,R)-trans 1,2-cyclohexanedicarboxylic acid. The (R,R)-trans 1,2-cyclohexane dicarboxylic acid obtained was esterified with ethanol and the obtained ester compound was reduced with vitride to provide (R,R)-1,2-bis(hydroxymethyl)cyclohexane followed by treatment with methane sulfonyl chloride to form (R,R)-1,2-bis(methanesulfonyloxymethyl)cyclohexane. The process requires large quantity of reducing agent viz., for reducing one 1 g of compound about 5 g of reducing agent is required which is not conducive for industrial production.

Chinese patent application no. CN 102952001 discloses a process for the preparation of (1R,2R)cyclohexane-1,2-dimethanol by the reduction of (1R,2R)cyclohexane-1,2-dicarboxylic acid using sodium borohydride or potassium borohydride and boron triflouoride diethyl ether in THF or diethyl ether as solvent. Boron triflouoride diethyl ether is used in large quantity and quite expensive which makes the process commercially unviable.

International publications no. WO 2012/131606 and WO 2014/037886 disclose a process for preparation of lurasidone which involves separating the racemic trans1,2-cyclohexane dicarboxylic acid into its (R,R) trans and (S,S) trans isomers and then using the desired trans (R,R) isomer for the preparation of lurasidone hydrochloride using the chemistry disclosed in U.S. Pat. No. 5,532,372 for preparation of racemic lurasidone hydrochloride. In these publications diisobutyl aluminium hydride (DIBAL) is used as the reducing agent for the preparation of (1R,2R) cyclohexane 1,2-dimethanol from (1R,2R) cyclohexane 1,2-dicarboxylic acid which is quite expensive. Further the process involves the usage of dibenzo-18-crown-6-ether as a phase transfer catalyst which is costly material and in turn increases the cost of production.

Some of the prior art processes disclose the process for the preparation of lurasidone hydrochloride from 1,2-(1R,2R)-bis-(methanesulfonyloxymethyl)cyclohexane using different solvents and bases.

U.S. Pat. No. 8,853,395 discloses a process for the preparation of lurasidone in which condensation of trans-1,2-bis(methanesulfonyloxymethyl)cyclohexane with 1-(1,2- benz isothiazol-3-yl)piperazine and condensation of trans-3a,7a-octahydroisoindolium-2-spiro-1'-[4'-(1,2-benzisothiazol-3-yl)]piperazine methanesulfonate with bicyclo[2.2.1]heptane-2-exo-3-exo-dicarboximide is carried out using organic bases with a $pK_b$ higher than 10 such as 1,4-diazabicycloundec-7-ene (DBU), 1,5-diazabicyclo[4.3.0]non-5-ene (DBN), 1,4-diaza bicyclo[2.2.2]-octane (DABCO). These organic bases are comparatively expensive.

Indian patent application no. IN 2306/MUM/2014 and Chinese patent applications no. CN 102863437 and CN 103864774 disclose the use of dimethyl formamide (DMF), dimethyl sulphoxide (DMSO), dimethyl acetamide (DMA) and N-methyl pyrrolidine (NMP) for the condensation of trans-3a,7a-octahydroisoindolium-2-spiro-1'-[4'-(1,2-benzisothiazol-3-yl)]piperazine methanesulfonate with bicyclo[2.2.1] heptane-2-exo-3-exo-dicarboximide to form lurasidone. These solvents have high boiling point so not preferred at commercial scale.

Some of the prior art processes are related to reduction of impurities or quality improvement of lurasidone hydrochloride.

International publication no. WO2011/136383 discloses a process for the preparation of lurasidone hydrochloride in which amount of by products are reduced by increasing the quantity of 1-(1,2-benzisothiazol-3-yl)piperazine instead of sodium carbonate or potassium carbonate as base in the reaction mixture. Increasing the amount of 1-(1,2-benzisothiazol-3-yl)piperazine causes an increase in cost of production and removal of excess compound makes the process less commercially viable.

International publication no. WO2011/136384 discloses a process for the preparation of lurasidone hydrochloride in which amount of by products are reduced by using dibasic potassium phosphate with a small amount of water as a base instead of sodium carbonate. Use of dibasic potassium phosphate as a base causes an increase in cost of production as dibasic potassium phosphate is expensive.

International publication no. WO2013/014665 discloses various processes for the preparation of lurasidone hydrochloride. In general the process is shown below:

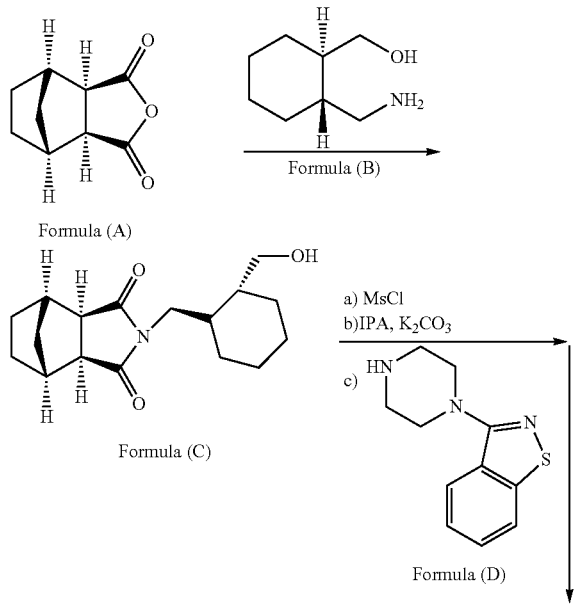

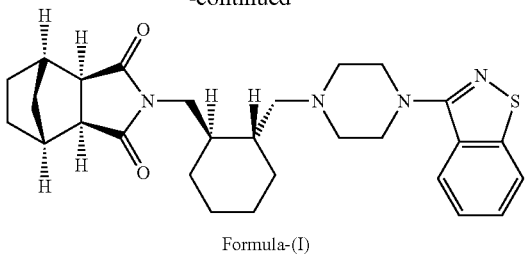

Formula-(I)

In this process trans-(1R,2R)-2-(aminomethyl)cyclohexyl)methanol of Formula (B) is first reacted with bicyclo [2.2.1]heptane-2-exo-3-exo-dicarboximide of Formula (A) to form (3aR,4S,7R,7aS)-2-(((1R,2R)-2-(hydroxymethyl)cyclohexyl)methyl)hexahydro-1H-4,7-methanoisoindole-1,3(2H)-dione of Formula (C) which on reaction with methane sulphonyl chloride followed by reaction with 1-(1,2-benzisothiazol-3-yl)piperazine of Formula (D) forms lurasidone free base which was converted into lurasidone hydrochloride using acetone and conc. hydrochloric acid.

Some of the prior art processes disclose various combinations of hydrogen chloride and solvent for the preparation of lurasidone hydrochloride from lurasidone free base.

U.S. Pat. No. 7,605,260 discloses use of acetone and aqueous HCl having strength 1.8-14.4% for preparing lurasidone hydrochloride. The yield of lurasidone hydrochloride is relatively low (85%) by this method. If the acid concentration during the salt formation is more than 5.0% then acetone quantity as the residual solvent in the reaction product is found to be greater than 0.5% in our hands which is above the ICH limits. If acid concentration during the salt formation is less than 1.8%, then yield is reduced drastically to 65%. Therefore, this method has limitations on the large-scale industrial production.

Chinese patent application no. CN102746289A discloses the process for the preparation of lurasidone hydrochloride by adding a mixture of acetone and aqueous HCl to a solution of lurasidone free base in acetone. On reproducing this process in laboratory, it was observed that the XRPD of the product obtained does not match with XRPD of lurasidone hydrochloride.

Indian patent application IN 777/MUM/2013 discloses use of IPA, water and 35% Aqueous HCl for the preparation of lurasidone hydrochloride. The IPA content in the product was found to be more than 5000 ppm.

The methods described in the prior art are not suitable for large scale commercial production as the residual solvent is out of the ICH limits and thus the product obtained can't be used as a drug. In order to keep the residual solvent(s) within ICH limits, repeated crystallization/purification are required which results in reduced yield and make the process quite expensive.

The prior art discloses various processes for the preparation of lurasidone hydrochloride and its intermediates. However, there still remains a need for alternative process for the preparation of lurasidone and its pharmaceutically acceptable salts substantially free of residual solvent(s) which can be used as a drug.

SUMMARY OF THE INVENTION

A principal object of the present invention is to provide an improved process for the preparation of Lurasidone and pharmaceutically acceptable salts thereof via novel compound of Formula (IV) which is used as an antipsychotic agent useful for the treatment of schizophrenia and bipolar disorder.

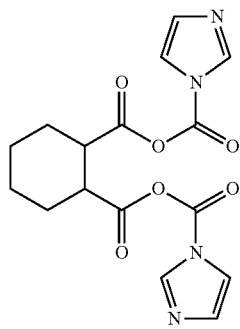

Formula-(III)

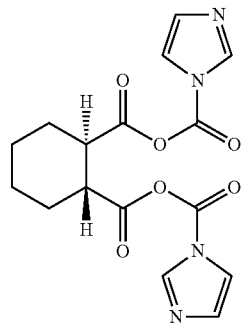

Formula (V)

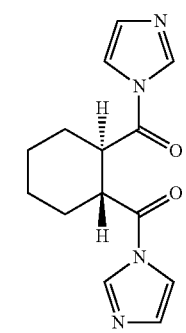

Formula (VI)

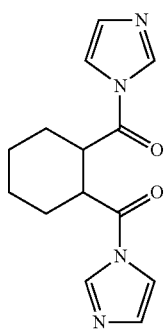

Formula-(IV)

It is another object of the present invention to provide a process for the preparation of the novel compound of Formula (IV), which is cost effective and industrially amenable.

It is another object of the present invention, to provide the use of novel compound of Formula (IV) for the preparation of compound of Formula (VII), their isomers and pharmaceutically acceptable salts thereof.

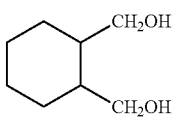

Formula (VII)

It is another object of the present invention to provide a process, wherein the novel compound of Formula (VI) is used as an intermediate to produce lurasidone hydrochloride of Formula (I).

It is another object of the present invention, to provide the use of novel compound of Formula (VI) for the preparation of lurasidone and its pharmaceutically acceptable salts thereof.

It is another object of the invention to provide a crystalline lurasidone hydrochloride, substantially free of residual solvent.

It is another object of the invention to provide a cost effective and commercially viable process for the preparation of lurasidone hydrochloride substantially free of residual solvent.

It is another object of the present invention to provide a process for the de-solvent treatment of lurasidone hydrochloride having higher content of residual solvent(s) by converting into free base and isolated. This isolated free base is converted into hydrochloride salt by the process of the present invention to provide lurasidone hydrochloride substantially free of residual solvent which can be used as a drug.

Other aspects will be set forth in the description which follows, and in part will be apparent from the description or may be learnt by the practice of the invention.

DETAILED DESCRIPTION OF THE INVENTION

While this specification concludes with claims particularly pointing out and distinctly claiming that, which is regarded as the invention, it is anticipated that the invention can be more readily understood through reading the following detailed description of the invention and study of the included examples.

The present invention relates to a process for the preparation of lurasidone or pharmaceutically acceptable salt thereof comprising the steps of:

a) converting ((R,R)-cyclohexane-1,2-diyl)bis((1H-imidazol-1-yl)methanone) to trans(R,R)-1,2-bis(hydroxymethyl)cyclohexane, b) converting trans(R,R)-1,2-bis(hydroxymethyl)cyclohexane obtained in step (a) to Lurasidone and c) optionally converting Lurasidone free base into its pharmaceutically acceptable salt.

The present invention relates to novel compound of the Formula (IV), their isomers and pharmaceutically acceptable salts thereof, which are used as an intermediate for the production of antipsychotic agent useful for the treatment of schizophrenia and bipolar disorder.

According to one of the embodiment of the present invention, the compounds of the present invention include isomers. Isomers refer to molecules with the same chemical Formula but different chemical structures i.e. isomers contain the same number of atoms of each element, but have different arrangements of atoms in space. There are two main forms of isomers namely structural isomers and stereo isomers. The "structural isomers" refers to those compounds in which atoms and functional groups are joined together in different ways. Structural isomers have different IUPAC names and may or may not belong to the same functional group. Structural isomers include chain isomers, position isomers, functional isomers and tautomers. The "stereo isomers" refers to those compounds in which the bond structure is same, but the geometrical positioning of atoms and functional groups in space is different. Stereo isomers include enantiomers, diastereomers, geometrical isomers and conformational isomers.

The present invention also relates to a novel process for the preparation of the novel compound of Formula (IV), their isomers and pharmaceutically acceptable salts thereof.

According to another embodiment of the present invention, novel process for the preparation of the compound of Formula (III), their isomers and pharmaceutically acceptable salts thereof, comprises condensing 1,2-cyclohexane dicarboxylic acid of Formula (II), their isomers with carbonyl diimidazole, optionally in a solvent.

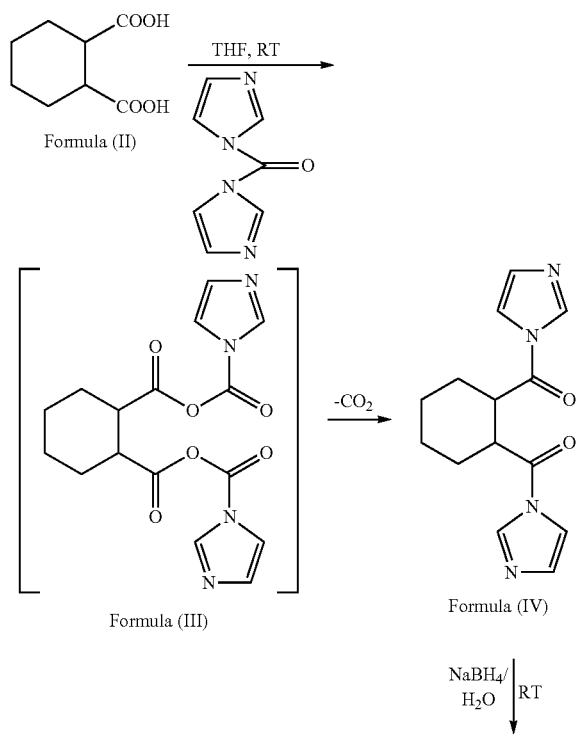

Formula (II), Formula (III), Formula (IV)

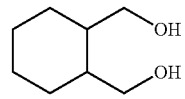

Formula (VII)

The condensation reaction of 1,2-cyclohexane dicarboxylic acid of Formula (II), their isomers with carbonyl diimidazole is carried out in the temperature range of 0° C. to 60° C., preferably in the temperature range of 25° C. to 30° C.

According to one other embodiment of the present invention, the novel process for the preparation of compound of Formula (IV), their isomers and pharmaceutically acceptable salts thereof, comprises decarboxylation of the likely intermediate compound of Formula (III). Without binding the invention by the theory, the compound of Formula (IV) can be formed via the intermediate compound of Formula (III), which inturn can be obtained from compound of Formula (II). The decarboxylation reaction may be very facile and it may not be possible to isolate the compound of Formula (III).

The decarboxylation of compound of Formula (III) is carried out in the temperature range of 0° C. to 55° C., optionally in the presence of solvent.

The solvent used herein include, but is not limited to, alcohols, ketones, alkyl acetates, chlorinated hydrocarbons, ethers, nitriles or hydrocarbons. Examples of alcohols include, but are not limited to, methanol, ethanol, n-propanol, iso-propanol, n-butanol, iso-butanol, sec-butanol, tert-butanol, n-pentanol, iso-pentanol, sec-pentanol, tert-pentanol and mixtures thereof; Examples of ketones include, but are not limited to, acetone, methyl ethyl ketone, methyl isobutyl ketone and mixtures thereof; Examples of alkyl acetates include, but are not limited to, ethyl acetate, methyl acetate, butyl acetate, isopropyl acetate and mixtures thereof; Examples of chlorinated hydrocarbons include, but are not limited to, dichloromethane, chloroform and mixtures thereof; Examples of ethers include, but are not limited to, diethyl ether, diisopropyl ether, methyl butyl ether, tetrahydrofuran, dioxane and mixtures thereof; Examples of nitriles include, but are not limited to, acetonitrile, propionitrile and mixtures thereof; Examples of hydrocarbons include, but are not limited to, benzene, xylene, toluene, hexanes, n-hexane, n-hetane, heptanes, pentane, cyclohexane, cyclopentane and mixtures thereof. Preferred solvents are THF, dioxane, cyclohexane and the mixtures thereof.

The present invention also relates to the use of the novel compound of Formula (IV), their isomers and pharmaceutically acceptable salts thereof, for the preparation of compound of Formula (VII), their isomers and pharmaceutically acceptable salts thereof.

According to yet another embodiment of the present invention, the process for the preparation of compound of Formula (VII) comprises reduction of compound of Formula (IV) with a suitable reducing agent. The reducing agent used herein include, but is not limited to, diisobutyl aluminum hydride, lithium aluminium hydride, vitride, lithium borohydride, sodium borohydride, calcium borohydride, and lithium triethylborohydride and mixtures thereof. Preferred reducing agent is sodium borohydride.

The compound of Formula (IV) is reduced into compound of Formula (VII), optionally in the presence of solvent. The solvent used herein include, but is not limited to, hydrocarbons or ethers. Examples of hydrocarbons include, but are not limited to, benzene, xylene, toluene, hexane, heptanes, pentane, cyclohexane, cyclopentane and mixtures thereof. Examples of ethers include, but are not limited to, diethyl ether, diisopropyl ether, methyl butyl ether, tetrahydrofuran, dioxane and mixtures thereof. Preferred solvents are THF, dioxane and the mixtures thereof.

The reducing agent is added lot-wise or in one lot. The reduction is carried out in the temperature range of 10° C. to 80° C., preferably in the range of 20° C. to 50° C., more preferably in the range of 20° C. to 30° C.

According to another embodiment of the present invention, the compound of Formula (VII) can also be prepared in one pot from the compound of Formula (II) without isolation of the intermediates.

According to one of the preferred embodiment of the present invention, there is provided novel compound of Formula (V) and its pharmaceutically acceptable salts thereof, and Formula (VI) and its pharmaceutically acceptable salts thereof, process for their preparation and use thereof for the production of lurasidone and its pharmaceutically acceptable salts thereof.

According to another preferred embodiment of the present invention, the novel process for the preparation of the compound of Formula (V) and its pharmaceutically acceptable salts thereof, comprises condensing trans(R,R)-1,2-cyclohexane dicarboxylic acid with carbonyl diimidazole optionally in a solvent. The condensation is carried out in the temperature range of 0° C. to 60° C., preferably in the temperature range of 0° C. to 35° C., more preferably in the range of 20° C. to 30° C.

trans(R,R)-1,2-cyclohexane dicarboxylic acid used as starting compound is prepared by the processes known in the prior art.

According to another preferred embodiment of the present invention, the novel process for the preparation of compound of Formula (VI) and its pharmaceutically acceptable salts thereof, comprises decarboxylation of the likely compound of Formula (V) optionally in a solvent. The decarboxylation is carried out in the temperature range of 0° C. to 55° C., preferably in the temperature range of 0° C. to 35° C., more preferably in the range of 20° C. to 30° C.

According to another preferred embodiment of the present invention, there is provided a process for the preparation of lurasidone hydrochloride and its intermediates, as shown in scheme-1.

Scheme-1:

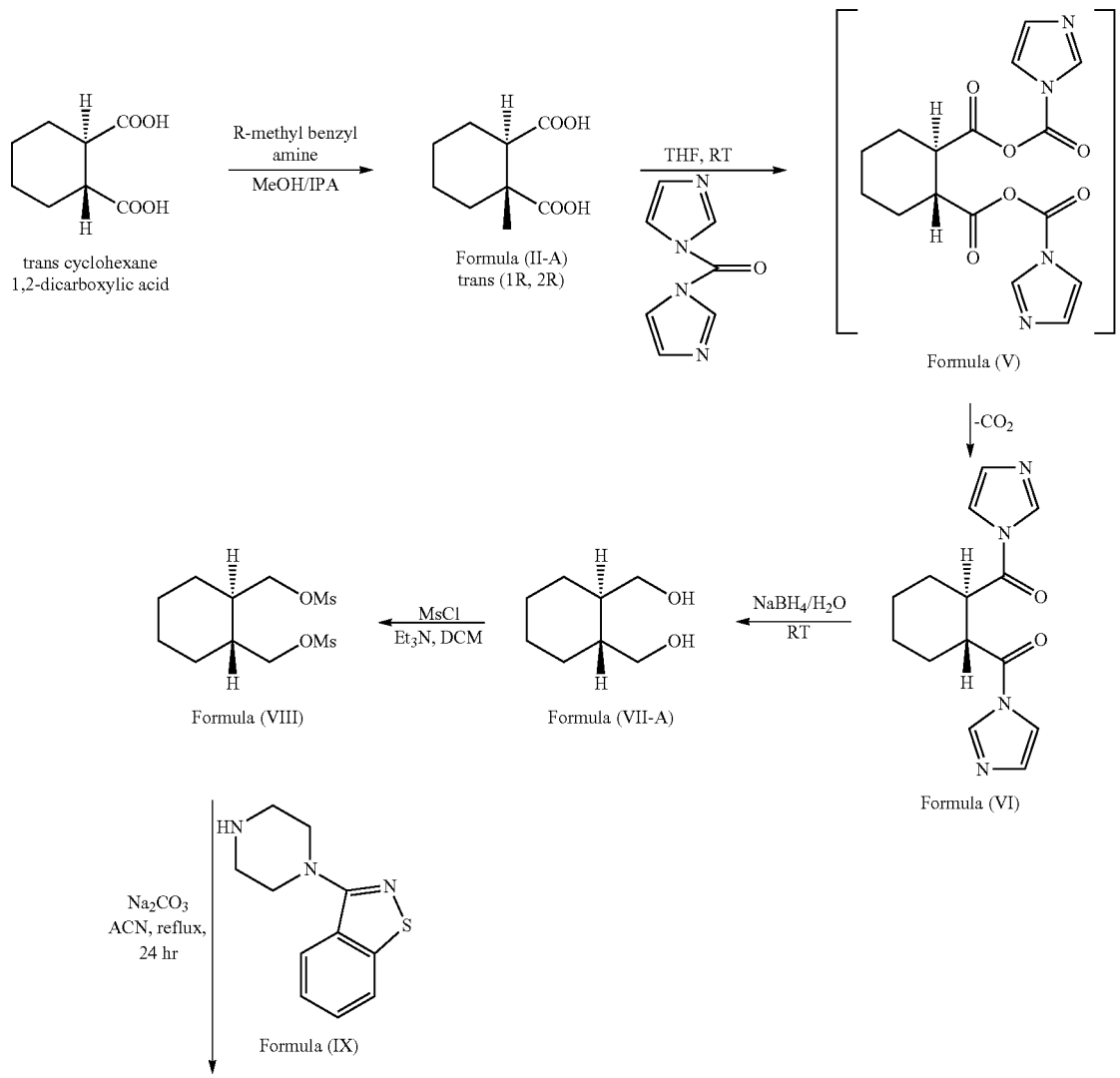

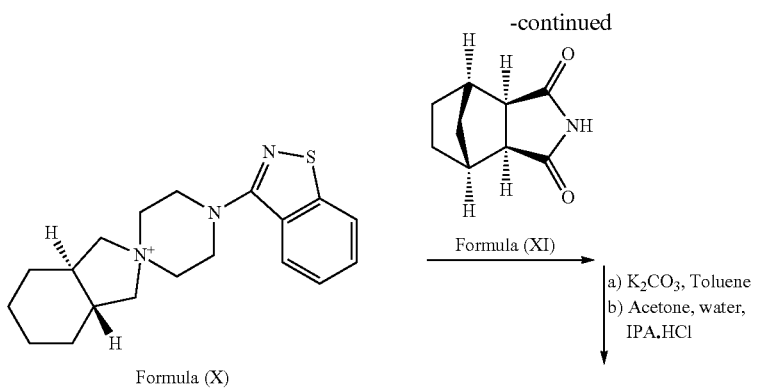

Formula (X)

-continued

Formula (XI)

a) K₂CO₃, Toluene
b) Acetone, water, IPA.HCl

Formula (I)

Without binding the invention by the theory, the compound of Formula (VI) can be formed via the intermediate compound of Formula (V), which inturn can be obtained from compound of Formula (II-A). The decarboxylation reaction may be very facile and it may not be possible to isolate the compound of Formula (V).

According to another embodiment of the present invention, there is provided a novel process for the preparation of trans(R,R)-1,2-bis(hydroxymethyl)cyclohexane of formula (VII-A). The process comprises condensing trans(R,R)-1,2-cyclohexane dicarboxylic acid with carbonyl diimidazole to get likely intermediate compound of Formula (V), which on decarboxylation, form compound of Formula (VI). Reducing the compound of Formula (VI) using a suitable reducing agent, optionally in a solvent resulted in the formation of trans(R,R)-1,2-bis(hydroxymethyl)cyclohexane of formula (VII-A).

The reducing agent used herein include, but is not limited to, diisobutyl aluminum hydride, lithium aluminium hydride, vitride, lithium borohydride, sodium borohydride, calcium borohydride, and lithium triethylborohydride. Preferred reducing agent is sodium borohydride.

The solvent used herein include, but is not limited to, hydrocarbons or ethers. Examples of hydrocarbons include, but are not limited to, benzene, xylene, toluene, hexane, heptanes, pentane, cyclohexane, cyclopentane and mixtures thereof. Examples of ethers include, but are not limited to, diethyl ether, diisopropyl ether, methyl butyl ether, tetrahydrofuran, dioxane and mixtures thereof. Preferred solvents are THF, dioxane and the mixtures thereof.

The reducing agent is added drop-wise or in one lot. The reduction is carried out in the temperature range of about 10° C. to 80° C., preferably in the temperature range of about 0° C. to 30° C., more preferably in the temperature range of about 20° C. to 30° C.

According to one other preferred embodiment of the present invention, there is provided a one pot process for the preparation of trans(R,R)-1,2-bis(hydroxymethyl)cyclohexane from trans(R,R)-1,2-cyclohexane dicarboxylic acid without isolation of the intermediates.

According to another preferred embodiment of the present invention, there is provided a novel process for the preparation of trans(R,R)-1,2-bis(methanesulfonyloxymethyl) cyclohexane of formula (VIII) comprising the steps of:

a) condensing trans(R,R)-1,2-cyclohexane dicarboxylic acid with carbonyl diimidazole to obtain the compound of Formula (VI);

b) reducing compound of Formula (VI) with a suitable reducing agent to form trans(R,R)-1,2-bis(hydroxymethyl)cyclohexane;

c) reacting trans(R,R)-1,2-bis(hydroxymethyl)cyclohexane with sulfonyl chloride optionally in the presence of a base and a solvent to form trans(R,R)-1,2-bis(methanesulfonylmethyl)cyclohexane of formula (VIII).

The sulphonyl chloride used in sulphonation include, but is not limited to, alkyl- or aryl-sulphonyl chloride selected from the group comprising of methane sulphonyl chloride, ethane sulphonyl chloride, p-toluene sulphonyl chloride, benzene sulphonyl chloride and mixtures thereof, preferably methane sulphonyl chloride is used.

The base used in step (c) herein includes, but is not limited to, organic or inorganic base. Examples of organic bases include, but are not limited to, triethylamine, ammonia, isopropyl ethyl amine, propyl ethyl amine, ethanolamine, chloramines, piperidine, pyridine, their salts and mixture thereof. Examples of inorganic bases include, but are not limited to, hydroxides, carbonates and bicarbonates of alkali and alkaline earth metals such as sodium carbonate, potassium carbonate, calcium carbonate, magnesium carbonate, sodium bicarbonate, potassium bicarbonate, lithium hydroxide, sodium hydroxide, potassium hydroxide and mixtures thereof.

The solvent used in step (c) herein include, but is not limited to, ether, chlorinated solvents, basic solvents. Examples of ether solvents include, but are not limited to, tetrahydrofuran, diethyl ether, ethyl propyl ether, methyl ethyl ether and mixtures thereof. Examples of chlorinated solvents include, but are not limited to, dichloromethane, chloroform and mixtures thereof. Examples of basic solvents include, but are not limited to, pyridine, piperidine, alpha picoline, gamma picoline and mixtures thereof.

According to another preferred embodiment of the present invention, there is provided a novel process for the preparation of trans(R,R)-3a,7a-octahydroisoindolium-2-spiro-1'-[4-(1,2-benzoisothiazole-3-yl)]piperazine methanesulfonate comprising the steps of:
- a) condensing trans(R,R)-1,2-cyclohexane dicarboxylic acid with carbonyl diimidazole to obtain compound of Formula (VI);
- b) reducing compound of Formula (VI) to form trans(R,R)-1,2-bis(hydroxymethyl)cyclohexane;
- c) reacting trans(R,R)-1,2-bis(hydroxymethyl)cyclohexane with sulfonyl chloride optionally in the presence of a base and a solvent to form trans(R,R)-1,2-bis(methanesulfonylmethyl)cyclohexane;
- d) reacting trans(R,R)-1,2-bis(methanesulfonylmethyl)cyclohexane with 3-(1-piperazinyl-1,2-benzisothiazole) optionally in the presence of a base and a solvent to form trans(R,R)-3a,7a-octahydroisoindolium-2-spiro-1'-[4-(1,2-benzo isothiazole-3-yl)]piperazine methanesulfonate.

The solvent used in step (d) herein include, but is not limited to, alcohol, nitrile or amide solvent. Examples of alcohol solvents include, but are not limited to, methanol, ethanol, propanol, iso-propanol, butanol, iso-butanol, tert-butanol, pentanol, iso-pentanol and mixtures thereof. Examples of nitriles include, but are not limited to, acetonitrile, propionitrile and mixtures thereof. Examples of amide solvents include, but are not limited to, N,N-dimethyl formamide, N,N-diethylformamide and mixtures thereof.

The base used in step (d) herein include, but is not limited to, carbonates, bicarbonates and hydroxides of alkali and alkaline earth metals such as sodium carbonate, potassium carbonate, calcium carbonate, magnesium carbonate, sodium bicarbonate, potassium bicarbonate, lithium hydroxide, sodium hydroxide, and potassium hydroxide and mixtures thereof.

According to another preferred embodiment of the invention, there is provided a novel process for the preparation of lurasidone or pharmaceutically acceptable salt thereof according to claim 1, comprising the steps of:
- a) condensing trans(R,R)-1,2-cyclohexane dicarboxylic acid with carbonyl diimidazole to obtain ((R,R)-cyclohexane-1,2-diyl)bis((1H-imidazol-1-yl)methanone);
- b) reducing ((R,R)-cyclohexane-1,2-diyl)bis((1H-imidazol-1-yl)methanone) to form trans(R,R)-1,2-bis(hydroxymethyl)cyclohexane;
- c) reacting trans(R,R)-1,2-bis(hydroxymethyl)cyclohexane with sulfonyl chloride optionally in the presence of a base and a solvent to form trans(R,R)-1,2-bis(methanesulfonylmethyl)cyclohexane;
- d) reacting trans(R,R)-1,2-bis(methanesulfonylmethyl)cyclohexane with 3-(1-piperazinyl-1,2-benzisothiazole) optionally in the presence of a base and a solvent to form trans(R,R)-3a,7a-octahydroisoindolium-2-spiro-1'-[4-(1,2-benzo isothiazole-3-yl)]piperazine methanesulfonate;
- e) reacting (3aR,7aR)-4-(benzo[d]isothiazolyl)octahydrospiro[isoindole-2,1-piperazin]-1-ium methanesulfonate with bicycle[2.2.1]heptanes-2-exo-3-exo-dicarboximide optionally in the presence of a base, solvent and phase transfer catalyst to form lurasidone free base;
- f) isolating lurasidone free base and
- g) optionally converting lurasidone free base into its pharmaceutically acceptable salt.

The base used in step (e) herein include, but is not limited to, carbonates, bicarbonates and hydroxides of alkali and alkaline earth metals such as sodium carbonate, potassium carbonate, calcium carbonate, magnesium carbonate, sodium bicarbonate, potassium bicarbonate, lithium hydroxide, sodium hydroxide, and potassium hydroxide and mixtures thereof.

The solvent used in step (e) herein include, but is not limited to, benzene, xylene, toluene, hexane, heptanes, pentane, cyclohexane, cyclopentane and mixtures thereof.

The catalyst used in step (e) herein include, but is not limited to, tetramethyl ammonium bromide, tetramethyl ammonium chloride, tetramethyl ammonium iodide, benzyl tributyl ammonium bromide, 1-methylpyridinium iodide, trimethylcyclopropyl, tetramethyl-2-butylammonium chloride and dibenzo-18-crown-6 ether.

According to the present invention, the process for the preparation of lurasidone hydrochloride substantially free of residual solvent (s) comprising the following steps:
- a) adding lurasidone free base to a water miscible solvent
- b) adding water to the mixture of step a);
- c) optionally heating the mixture of step b);
- d) adding alcoholic solution of hydrogen chloride;
- e) isolating lurasidone hydrochloride.

Water miscible organic solvent used herein include, but is not limited to, ketone, alcohol, ether, nitrile like acetone, methyl ethyl ketone, methanol, ethanol, 1-propanol, 2-propanol, ethylene glycol, propylene glycol, 1,3-propanediol, 1,5-pentanediol, 1,2-butanediol, 1,3-butanediol, 1,4-butanediol, 2-butoxyethanol, THF, acetonitrile and the mixtures thereof.

Water miscible solvent is used in an amount of 3 to 50 times (by weight) of lurasidone free base, preferably in an amount of 10 to 30 times by lurasidone free base, more preferably in an amount of 15 to 20 times by lurasidone free base.

Water is used in an amount of 0.1 to 5 times (by weight) of the amount of lurasidone free base, preferably in an amount of 0.4 to 3 times by weight of lurasidone free base, more preferably in an amount of 0.8 to 2.0 times by weight of lurasidone free base.

The temperature for dissolving the lurasidone free base in a mixture of water and water miscible solvent is usually in the range of 0° C. to a reflux temperature, preferably in the range of 20° C. to a reflux temeperature, more preferably in the range of 55° C. to a reflux temperature.

Alcoholic solution of hydrogen chloride used herein include, but is not limited to, methanolic HCl, ethanolic HCl, IPA.HCl. Preferably IPA.HCl is being used.

The strength of hydrogen chloride in alcoholic hydrogen chloride is in the range of 5-25% w/w, preferably in the range of 10-20% w/w.

The temperature during the addition of HCl to solution of compound of formula (II) is usually in the range of 0° C. to a reflux temperature, preferably in the range of 55° C. to a reflux temperature. Preferably the solution has to be clear during HCl addition.

The base used in the present invention, is selected from the group consisting of organic base, inorganic base and mixtures thereof. Inorganic base used herein is preferably selected from the group consisting of sodium bicarbonate, potassium bicarbonate, sodium carbonate, potassium carbonate, sodium hydroxide, potassium hydroxide or the like. The most preferred inorganic bases are sodium bicarbonate or potassium bicarbonate.

The organic base may be selected from the group comprising of $C_1$-$C_4$ alkyl ammonia; mono, di or tri $C_1$-$C_4$ alkyl amine such as triethyl amine, diisopropyl ethyl amine; mono, di or tri hydroxyl $C_1$-$C_4$ alkyl amine; morpholine, pyridine, piperidine and pyrrolidine.

The crystals of the lurasidone hydrochloride compound of formula (I) precipitated are separated by a conventional method, for example, by filtration.

According to another preferred embodiment of the invention, there is provided a process for the preparation of lurasidone hydrochloride substantially free of residual solvent (s) comprising the following steps:
a) adding lurasidone free base to acetone;
b) adding water to the suspension of step (a);
c) heating the mixture of step (b);
d) adding isopropanolic solution of hydrogen chloride;
e) isolating lurasidone hydrochloride.

According to another embodiment of the invention, there is provided the use of compound of Formula (IV), their isomers and pharmaceutically acceptable salts thereof, for the preparation of 1,2-bis(hydroxymethyl)cyclohexane.

According to another preferred embodiment of the invention, there is provided the use of compound of Formula (VI) and its pharmaceutically acceptable salts thereof, for the preparation of trans(R,R)-1,2-bis(hydroxymethyl)cyclohexane.

According to another preferred embodiment of the invention, there is provided the use of compound of Formula (VI) and its pharmaceutically acceptable salts thereof, for the preparation of trans(R,R)-1,2-bis(methanesulfonylmethyl)cyclohexane.

According to another preferred embodiment of the invention, there is provided the use of compound of Formula (VI) and its pharmaceutically acceptable salts thereof, for the preparation of trans(R,R)-3a,7a-octahydroisoindolium-2-spiro-1'-[4-(1,2-benzoisothiazole-3-yl)]piperazine methanesulfonate.

According to another preferred embodiment of the invention, there is provided the use of compound of Formula (VI) and its pharmaceutically acceptable salts thereof, for the preparation of lurasidone and its pharmaceutically acceptable salts thereof.

According to another preferred embodiment of the invention, there is provided a pharmaceutical composition comprising Lurasidone, or a pharmaceutically acceptable salt thereof prepared by process of present invention and a pharmaceutically acceptable carrier.

The present invention is further illustrated below with reference to the following examples without intending to limit the scope of the invention in any manner.

Example-1

Synthesis of trans(R,R)-1,2-cyclohexane dicarboxylic acid

A round bottom flask was charged with methanol (500 mL), IPA (500 mL) and trans (racemic)-1,2-cyclohexane dicarboxylic acid (100 g). In this reaction mass (R)-1-phenylethyl amine (74 mL) was added over a period of 30 minutes and stirred for 2-3 hrs at 30-40° C. The solid obtained was filtered, washed with methanol and IPA solution (50+50 mL) and dried under reduced pressure to obtain crude salt of trans(R,R)-1,2-cyclohexane dicarboxylic acid. The obtained salt was stirred in a solution of methanol (500 mL) and IPA (500 mL) at 65-70° C. for 2-3 hours, cooled to room temperature and filtered. The solid was washed with methanol and IPA solution (50+50 mL) and dried under reduced pressure. The solid thus obtained was dissolved in about 2N hydrochloric acid and extracted two times with ethyl acetate (1000 mL+200 mL). Organic layers were combined and washed with brine solution (100 mL). Ethyl acetate was distilled off under vacuum at 50-55° C. and cyclohexane was added to the residue. The solid separated out was filtered and washed with cyclohexane and dried under vacuum at 45-50° C. for 8-10 hours. Yield=29.4 g Example-2

Synthesis of ((R,R)-cyclohexane-1,2-diyl)bis((1H-imidazol-1-yl)methanone)

To a solution of trans(R,R)-1,2-cyclohexane dicarboxylic acid (25.0 g) in THF (250 mL), carbonyl diimidazole (60 g) is added and stirred for one hour at 25-30° C. To the said solution of (R,R)2-(((1H-imidazole-1carbonyl)oxy)carbonyl)cyclohexanecarboxylic acetic anhydrideIH-imidazole (25.0 g) in THF (250 mL) is stirred for one hour at 45-50° C. The compound obtained is isolated and is characterized by mass and NMR.

[m/z=272.75; $^1$H-NMR: 8.24 (s, 2H), 7.72 (d, 2H); 7.50 (d, 2H), 3.5 (m, 2H), 2.26-1.50 (m, 8H)]

Example-3

Synthesis of trans(R,R)-1,2-bis(hydroxymethyl)cyclohexane

To a solution of ((R,R)-cyclohexane-1,2-diyl)bis((1H-imidazol-1-yl)methanone) (25 g) in THF (250 mL), sodium borohydride (22.0 g) followed by water (44.0 mL) are added and stirred for one hour. To this reaction mass, 10% solution of acetic acid (500 mL) and dichloromethane (500 mL) are added, stirred and layers separated. The organic layer is washed with 10% sodium bicarbonate solution followed by water. The dichloromethane is distilled off from organic layer under vacuum to give an oily mass. To the oily mass dichloromethane (100 mL), water (100 mL) and 12.5 mL conc. hydrochloric acid (35%) are added, stirred and layers obtained are separated. The dichloromethane is distilled off completely from organic layer at 40° C. to obtain oily mass (15.5 g).

Example-4

One Pot Process For Synthesis of trans(R,R)-1,2-bis(hydroxymethyl)cyclohexane from trans(R,R)-1,2-cyclohexane dicarboxylic acid To a solution of trans(R,R)-1,2-cyclohexane dicarboxylic acid (25.0 g) in THF (250 mL), carbonyl diimidazole (60 g) was added and stirred for one hour at 25-30° C. To the intermediate obtained sodium borohydride (22.0 g) and water (44.0 mL) were added and stirred for one hour. To this reaction mass, 10% solution of acetic acid (500 mL) and dichloromethane (500 mL) were added, stirred and layers separated. The aqueous layer was washed with dichloromethane (250 mL). The organic layer was washed with 10% sodium bicarbonate solution followed by water. The dichloromethane is distilled off from organic layer under vacuum to give an oily mass. To the oily mass dichloromethane (100 mL), water (100 mL) and 12.5 mL conc. hydrochloric acid (35%) were added, stirred and layers obtained were separated. The dichloromethane was distilled off completely at 40° C. to obtain oily mass (15.5 g).

Example-5

Synthesis of trans(R,R)-1,2-bis(methanesulfonylmethyl)cyclohexane

To a suspension of trans(R,R)-1,2-bis(hydroxymethyl) cyclohexane (15.0 g) in dichloro methane (300 mL), triethyl amine (43.7 mL) followed by methane sulphonyl chloride (17.8 mL) were added over a period of 30-45 minutes. Reaction mass was stirred for 2-3 hrs. Reaction was monitored by HPLC (RI detector). After the completion of reaction, water was added, stirred and layers separated. The organic layer was washed with 10% sodium bicarbonate solution (150 mL) followed by water (150 mL). The dichloromethane was distilled off from organic layer under vacuum at 40-55° C. to give an oily mass. Methanol (30 mL) was added to the oily mass and strip off under vacuum at 40° C., added methanol (150 mL) and stirred for 1 h at 10-15° C. and the solid obtained was filtered, washed with methanol (15 mL) and dried under vacuum to get the product (15.8 g).

Example-6

Synthesis of trans(R,R)-3a,7a-octahydroisoindolium-2-spiro-1'-[4-(1,2-benzoisothiazole-3-yl)] piperazine methanesulfonate To a suspension of trans(R,R)-1,2-bis(methanesulfonylmethyl)cyclohexane (15 g) in acetonitrile (150 mL) 1-(1,2-benzisothiazol-3-yl)piperazine (10.95 g) and sodium carbonate (7.8 g) were added, heated and stirred for 20 hrs at reflux temperature. Reaction was monitored by HPLC. After the completion of reaction, mass was cooled to 40-45° C., filtered and washed with acetonitrile (20 mL). The acetonitrile was distilled off under vacuum at 45-50° C. To the residue acetone (100 mL) was added, stirred for 1 hour, filtered, washed with acetone (10 mL), dried at 50-55° C. for 6-8 hours to get the product (12.5 g).

Example-7

Synthesis of Lurasidone

To a suspension of trans(R,R)-3a,7a-octahydroisoindolium-2-spiro-1'-[4-(1,2-benzo isothiazole-3-yl)]piperazinemethanesulfonate (10 g) in toluene (150 mL), bicycle [2.2.1]heptane-2-exo-3-exo-dicarboximide (5.9 g) and potassium carbonate (4.8 g) were added, heated to 110° C. and stirred for 8-10 hours. Reaction was monitored by HPLC. After the completion of reaction, reaction mass was cooled to 20-30° C., filtered and washed with toluene (10 mL). The toluene was distilled off at 55-60° C. To the residue IPA (100 mL) was added and stirred for 1-2 hours at room temperature. Lurasidone free base obtained was filtered and washed with IPA (10 mL). The solid was suck dried for 30 minutes to obtain lurasidone.

Example-8

Synthesis of Lurasidone hydrochloride

To lurasidone base (5 g), acetone (75 mL) and water (10 mL) were added. The mixture was heated to 55-60° C. followed by the addition of IPA.HCl (10%) (O1 mL) and stirred for 1-2 hours. reflux temperature. The clear solution obtained was stirred for 30 min and then 5 ml IPA.HCl (10%) was added. The reaction mixture was stirred at reflux temperature for 30 min, cooled and stirred for 60 min. The solid obtained was filtered and washed with acetone (5 ml) and dried under vacuum at 60° C. for 8 hours. Acetone: 542 ppm; IPA=38 ppm; Yield=93%

Example-9

Synthesis of Lurasidone hydrochloride

To lurasidone base (5 g), acetone (75 mL) and water (5 mL) were added. The mixture was heated to 55-60° C. followed by the addition of IPA.HCl (10%) (5 mL) and stirred for about 1-2 hours. The reaction mixture was stirred for 30 min. at 55-60° C., cooled and stirred for 60 min. The solid obtained was filtered and washed with acetone (5 ml) and dried under vacuum at 70-80° C. for 8 hours.

The invention claimed is:

1. A process for the preparation of lurasidone or a pharmaceutically acceptable salt thereof, comprising the steps of:
   a) converting ((R,R)-cyclohexane-1,2-diyl)bis((1H-imidazol-1-yl)methanone) to trans(R,R)-1,2-bis(hydroxymethyl)cyclohexane,
   b) converting trans(R,R)-1,2-bis(hydroxymethyl)cyclohexane obtained in step (a) to lurasidone, and
   c) optionally converting lurasidone free base into its pharmaceutically acceptable salt.

2. A process for the preparation of lurasidone or a pharmaceutically acceptable salt thereof according to claim 1, comprising the steps of:
   a) condensing trans(R,R)-1,2-cyclohexane dicarboxylic acid with carbonyl diimidazole to obtain ((R,R)-cyclohexane-1,2-diyl)bis((1H-imidazol-1-yl)methanone);
   b) reducing ((R,R)-cyclohexane-1,2-diyl)bis((1H-imidazol-1-yl)methanone) to form trans(R,R)-1,2-bis(hydroxymethyl)cyclohexane;
   c) reacting trans(R,R)-1,2-bis(hydroxymethyl)cyclohexane with sulfonyl chloride optionally in the presence of a base and a solvent to form trans(R,R)-1,2-bis(methanesulfonylmethyl)cyclohexane;
   d) reacting trans(R,R)-1,2-bis(methanesulfonylmethyl) cyclohexane with 3-(1-piperazinyl-1,2-benzisothiazole) optionally in the presence of a base and a solvent to form trans(R,R)-3a,7a-octahydroisoindolium-2-spiro-1'-[4-(1,2-benzo isothiazole-3-yl)]piperazine methanesulfonate;
   e) reacting (3aR,7aR)-4-(benzo[d]isotiazolyl)octahydrospiro[isoindole-2,1-piperazin]-1-ium methanesulfonate with bicycle[2.2.1]heptanes-2-exo-3-exo-dicarboximide optionally in the presence of a base, solvent and phase transfer catalyst to form lurasidone free base;
   f) isolating lurasidone free base and
   g) optionally converting lurasidone free base into its pharmaceutically acceptable salt.

3. A compound of ((R,R)-cyclohexane-1,2-diyl)bis((1H-imidazol-1-yl)methanone) of formula (VI):

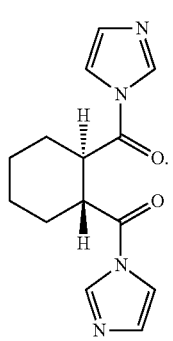
Formula (VI)
4. A method of preparing lurasidone comprising using the compound of claim 3.
\* \* \* \* \*